United States Patent [19]

Karatzas et al.

[11] Patent Number: 5,780,009
[45] Date of Patent: Jul. 14, 1998

[54] DIRECT GENE TRANSFER INTO THE RUMINANT MAMMARY GLAND

[75] Inventors: Constantinos Karatzas; Anthoula Lazaris-Karatzas, both of Beaconsfield; Jeffrey Donald Turner, Hudson, all of Canada

[73] Assignee: Nexia Biotechnologies, Inc., Quebec, Canada

[21] Appl. No.: 377,016

[22] Filed: Jan. 20, 1995

[51] Int. Cl.$^6$ .................... A61K 49/00; C12N 15/00; C12N 5/00; C12P 21/06
[52] U.S. Cl. .................... 424/9.1; 800/2; 800/DIG. 2; 935/60; 435/172.3; 435/69.1
[58] Field of Search .................... 800/2, DIG. 2; 435/172.3; 935/60; 424/9.1

[56] References Cited

U.S. PATENT DOCUMENTS

| | | | |
|---|---|---|---|
| 4,861,718 | 8/1989 | Hirata et al. | 435/207 |
| 4,873,316 | 10/1989 | Meade et al. | 530/412 |
| 5,047,340 | 9/1991 | Dickson et al. | 435/161 |
| 5,215,904 | 6/1993 | Gould et al. | 435/172.3 |
| 5,227,301 | 7/1993 | Turner et al. | 435/240.2 |
| 5,304,489 | 4/1994 | Rosen | 435/69.1 |
| 5,322,775 | 6/1994 | Clark et al. | |

FOREIGN PATENT DOCUMENTS

| | | | |
|---|---|---|---|
| 0 535 576 A1 | 4/1993 | European Pat. Off. | |
| 2 223 755 A | 4/1990 | United Kingdom | C12N 15/00 |
| WO 91/03551 | 3/1991 | WIPO | |
| WO 93/03709 | 3/1993 | WIPO | |
| WO 93/04165 | 3/1993 | WIPO | |
| WO 93/24640 | 12/1993 | WIPO | |
| WO 93/25567 | 12/1993 | WIPO | |
| WO 93/25673 | 12/1993 | WIPO | |
| WO 94/23050 | 10/1994 | WIPO | |
| PCT/CA96/00029 | 8/1996 | WIPO | |
| CA96/00029 | 2/1997 | WIPO | |

OTHER PUBLICATIONS

Hennighausen, L., "The Prospects for Domesticating Milk Protein Genes." *J. Cell. Bio.* 49: 325–332 (1992).
Romagnolo, D. et al., "Transgenic Approaches for Modifying the Mammary Gland to Produce Therapeutic Proteins," *Environmental Health Perspectives*, 102:846–51 (1994).
Yom, Heng-Cherl et al., Am.J.Clin.Nutr., vol. 58(2) Suppl., pp. 299S–306S, 1993.
Archer et al., "Human Growth Hormone (hGH) Secretion in Milk of Goats After Direct Transfer of the hGH gene into the Mammary Gland by Using . . . ", *Proc. Natl. Acad. Sci. USA*, 91:6840:6844 (1994).
Brown et al., "Mechanism of Membrane Anchoring Affects Polarized Expression of Two Proteins in MDCK cells," *Science*, 245:1499–1501 (1989).
Cannino et al., "Gene Expression of a Thermostable β-Galactosidase in Mammalian Cells and its Application in Assays of Eukaryotic Promoter Activity," *Biotechnol. Appl. Biochem.*, 19:233–244 (1994).

Collier et al., "Effect of Reserpine on Milk Production and Serum Prolactin of Cows Hormonally Induced into Lactation," *Journal of Dairy Science*, 60:896–901 (1976).
DiTullio et al., "Production of Cystic Fibrosis Transmembrane Conductance Regulator in the Milk of Transgenic Mice," *Bio/Technology*, 10:74–77 (1992).
Dong et al., "Efficient DNA Transfection of Quiescent Mammalian Cells using Poly-L-Orthine," *Nucleic Acids Research*, 21:771–772 (1993).
Eckhardt et al., "Characterization of the Promoter, Signal Sequence, and Amino Terminus of a Secreted β-Galactosidase from 'Streptomyces Lividans'", *Journal of Bacteriology*, 169:4249–4256 (1987).
Gorodetsky et al., "Isolation and Characterization of the Bos tauras β-casein Gene," *Gene*, 66:87–96 (1988).
Hubbes et al., "Human Placental β-Galactosidase," *Biochem. J.*, 285:827–831, (1992).
Jänne et al., "Transgenic Bioreactors," *Int. J. Biochem.*, 26:859–870 (1993).
Kalnis et al., "Sequence of the lacZ Gene of Escherichia Coli," *The EMBO Journal*, 2:593–597 (1983).
Kong et al., "Targeting of Recombinant Na+/glucose Cotransporter (SGLT1) to the Apical Membrane," *FEBS*, 333:1–4 (1993).
Kumar et al., "Saccharomyces Cerevisiae Cells Secreting an Aspergillus Niger β-Galactosidase Grow on Whey Permeate," *Bio/Technology*, 10:82–85 (1992).
Lee et al., "Production of Biomedical Proteins in the Milk of Transgenic Dairy Cows; the State of the Art," *Journal of Controlled Release*, 29:213–221 (1994).
Mantei et al., "Complete Primary Structure of Human and Rabbit Lactase-Phlorizin Hydrolase: Implications for Biosynthesis, Membrane Anchoring and Evolution of the Enzyme," *The EMBO Journal*, 7:2705–2713 (1988).

(List continued on next page.)

Primary Examiner—Deborah Crouch
Attorney, Agent, or Firm—Clark & Elbing LLP

[57] ABSTRACT

Disclosed is a method for expressing a heterologous gene in the mammary gland of a ruminant mammal. The invention is useful for producing a heterologous protein(s) in the milk of the mammal, for producing a heterologous enzyme(s) which is tethered to the mammary epithelial cell membrane and which can act on a component of the milk of the mammal, and for providing an antisense oligonucleotide(s) or ribozyme(s) which inhibits expression of a gene to a mammary epithelial cell. The method involves infusing a liquid complex including a genetic construct into a ductal tree of the mammal. The liquid complex can be infused before the mammal reaches sexual maturity and after the mammal develops a functional streak canal. Alternatively, a liquid complex that is free of live retroviruses can be infused. If desired, the infused genetic construct can be treated with a polycationic compound and/or a lipid to improve the efficiency with which it is taken up by an epithelial cell of the mammary gland.

41 Claims, 2 Drawing Sheets

OTHER PUBLICATIONS

Masibay et al., "Expression of Bovine β-1,4-galactosyltransferase cDNA in COS-7 Cells," *Proc. Natl. Acad. Sci. USA*, 86:5733-5737 (1989).

Masri et al., "Identification of the Full-Length Coding Sequence for Human Galactosyltransferase (β-N-Acetylglucosaminide: β1,4-Galactosyltransferase)," *Biochemical and Biophysical Res. Comm.* 157:657-663 (1988).

O'Leary et al., "A Comparison of Some Chemical Properties of Yogurts Made from Control and Lactase-Treated Milks," *Journal of Food Science*, 41:791-793 (1976).

Oshima et al., "Cloning, Sequencing, and Expression of cDNA for Human β-Galactosidase," *Biochemical and Biophysical Res. Comm.*, 157:238-244 (1988).

Poch et al., "Sequence of the Kluyveromyces lactis β-galactosidase: Comparison with Prokaryotic Enzymes and Secondary Structure Analysis," *Gene*, 118:55-63 (1992).

Rahim et al., "Production and Characterization of β-Galactosidase from Psychrotrophic Bacillus subtilis KL88," *Biotechnology and Applied Biochemistry*, 13:246-256 (1991).

Schmidt et al., "Expression and Nucleotide Sequence of the Lactobacillus bulgaricus β-Galactosidase Gene Cloned in Escherichia coli," *Journal of Bacteriology*, 171:625-635 (1989).

Schroeder et al., "Analysis of the lacZ sequences from two Streptococcus thermophilus strains: Comparison with Escherichia coli . . . ." *Journal of General Microbiology*, 137:369-380 (1991).

Shaper, et al. "Bovine Galactosyltransferase: Identification of a Clone by Direct Immunological Screening of a cDNA Expression Library," *Proc. Natl. Acad. Sci. USA*, 83:1573-1577 (1986).

Smith et al. "Hormone Induced Lactation in the Bovine. II. Response of Nulligravida Heifers to Modified Estrogen-Progesterone Treatment," *Journal of Dairy Science*, 57:296-303 (1973).

Sreekrishna et al., "Construction of Strains of Saccharomyces Cerevisiae that Grow on Lactose," *Proc. Natl. Acad. Sci. USA*, 82:7909-7913 (1985).

Violotte et al., "Complete Nucleotide Sequence of Bovine α-lactalbumin Gene: Comparison with its Rat Counterpart," *Biochimie*, 69:609-620 (1987).

Zhu, et al. "Systemic Gene Expression After Intravenous DNA Delivery into Adult Mice," *Science*, 261:209-211 (1993).

Felgner et al (1987) Proced. Natl. Acad. Sci. 84, 7413-7417.

DIRECT GENE TRANSFER INTO THE RUMINANT MAMMARY GLAND

BACKGROUND OF THE INVENTION

This invention relates to transferring a gene into a ruminant mammary gland.

A number of proteins have been produced by introducing transgenes with mammary-gland specific promoters into fertilized germ cells of animals and maintaining the animals such that the protein of interest is expressed in the milk of the mammal. Several methods for introducing DNA into somatic cells of animals have also been described. Such methods include direct injection of "naked" plasmid DNA or non-retroviral-based vectors carrying the transgene into tissues. Lipids have also been used to deliver transgenes to cells. The lipid-based methods can employ DNA molecules that are coupled to either ligand-specific compounds or cationic compounds that protect the DNA from degradation. Commercially available lipids, such as LIPOFECTIN™ (1:1 (w/w) DOTMA:DOPE), have been used to deliver genes into a variety of organs. Genes have been introduced into mammary glands of animals by methods such as those employing retroviral infection. For example, a human growth hormone (hGH) transgene has been expressed in the mammary glands of goats by infusing replication-defective retroviruses encoding hGH directly into the gland. Other methods for expressing heterologous genes in mammary cells include particle bombardment of mammary explants and organoids, and direct delivery of DNA by high-velocity helium-driven gas.

The ruminant mammary gland is a typical exocrine gland. The functional unit includes a single layer of columnar epithelial cells, while ducts are composed of a double layer of cuboidal epithelial cells. At two to five months of age, the bovine mammary gland is rudimentary. At begun to develop. The ductal system is composed of a small, central cistern and a simple, branched network of blind ducts which radiate from the cistern. The ducts terminate in groups of cells known as "buds" or "caps." Progenitor cells within the caps and ducts divide actively, allowing elongation of the ducts and formation of alveolar structures. By the age of 7 to 12 months, the ductal arbor is extensively branched with elongated ducts. In goats, the ductal system is relatively advanced at birth, with substantial branching present.

SUMMARY OF THE INVENTION

We have found that infusion of a genetic construct encoding a heterologous gene product into the ductal tree of the mammary gland of a ruminant mammal at an age earlier than sexual maturity and after development of a functional streak canal leading to the ductal tree results in production of the heterologous gene product in the mammary gland of the mammal.

Accordingly, the invention features, in one aspect, a method of producing, in a ruminant mammal, milk containing a heterologous protein. The method involves:

(a) providing a genetic construct including DNA encoding the heterologous protein and a signal peptide, (b) mixing the construct with a liquid carrier to form a liquid complex, (c) infusing the liquid complex into a ductal tree of the mammal at an age of the mammal earlier than sexual maturity and after development of a functional streak canal leading to the ductal tree, (d) raising the mammal so that the heterologous protein encoded by the construct is expressed and secreted into the milk produced by the ductal tree and the mammary alveolar cells, and (e) obtaining the milk from the mammal. The invention also features a composition which includes milk produced according to this method.

In another aspect, the invention features a method of producing, in a ruminant mammal, milk containing a heterologous protein, involving:

(a) providing a genetic construct including DNA encoding the heterologous protein and a signal peptide, (b) mixing the construct with a liquid carrier to form a liquid complex free of live retroviruses, (c) infusing the liquid complex into a ductal tree of the mammal, (d) raising the mammal so that the heterologous protein encoded by the construct is expressed and secreted into the milk produced by the ductal tree and the mammary alveolar cells, and (e) obtaining the milk from the mammal.

The invention also features, in another aspect, a method for expressing, in the mammary gland of a ruminant mammal, a heterologous enzyme which is tethered to the membrane of an epithelial cell of the mammary gland. The method involves:

(a) providing a genetic construct encoding the heterologous enzyme and a membrane-associated polypeptide, (b) mixing the construct with a liquid carrier to form a liquid complex, (c) infusing the liquid complex into a ductal tree of the mammal at an age of the mammal earlier than sexual maturity and after development of a functional streak canal leading to the ductal tree, and (d) raising the mammal so that the heterologous enzyme encoded by the construct is expressed and associated with the membrane of the epithelial cell.

The invention further features, in another aspect, a method of inhibiting expression of a gene in a mammary epithelial cell of a ruminant mammal. The method involves:

(a) providing a genetic construct encoding an antisense oligonucleotide, (b) mixing the construct with a liquid carrier to form a liquid complex, (c) infusing the liquid complex into a ductal tree of the mammal at an age of the mammal earlier than sexual maturity and after development of a functional streak canal leading to the ductal tree, and (d) raising the mammal so that the antisense oligonucleotide hybridizes to the gene in the mammary epithelial cell.

The invention also features a method for inhibiting expression of a gene in a mammary epithelial cell of a ruminant mammal. The method involves:

(a) providing a genetic construct encoding a ribozyme, (b) mixing the construct with a liquid carrier to form a liquid complex, (c) infusing the liquid complex into a ductal tree of the mammal at an age of the mammal earlier than sexual maturity and after development of a functional streak canal leading to the ductal tree, and (d) raising the mammal so that the ribozyme hydrolyzes the gene in the mammary epithelial cell.

In various embodiments, the mammal is bovine, a sheep, or a goat. If desired, a liquid complex that is free of live retroviruses can be infused into the mammal at an age earlier than sexual maturity and after development of a functional streak canal leading to the ductal tree. Virtually any heterologous protein accompanied by a signal peptide can be produced in the milk of the ruminant. If desired, the heterologous protein or tethered enzyme can be one which is enzymatically active on a component of milk. For example, the protein can be β-galactosidase capable of hydrolyzing at least 5% of the lactose in the milk. The gene encoding β-galactosidase can be derived from an organism such as *Aspergillus niger*, *Aspergillus oryzae*, *Bacillus stearothermophilus*, *Escherichia coli*, *Homo sapiens*, *Kluyveromyces lactis*, *Kluyveromyces fragilis*, *Lactobacillus bulgaricus*, *Streptococcus thermophilus*, *Streptomyces lividans*, *Bacillus subtilis*, or *Sulfolobus solfataricus*. Included in the invention is lactose-reduced milk produced in a ruminant mammal according to the invention.

In other embodiments, the heterologous protein is a tissue plasminogen activator (e.g., human tissue plasminogen activator (htPA)), a cytokine (e.g., an interleukin such as IL-6 or IL-2), an aspartic protease (e.g., aspartic proteases from *Rhizomucor nichei* or *Rhizomucor puscillus*), lysozyme, a stearyl-CoA desaturase, a lipase (e.g., a bile-activated lipase or carboxy ester lipase), galactosyltransferase, a blood clotting factor (e.g., factor I, II, III, IV, V, VII, VIII, IX, X, XI, XI, or XIII), a growth factor (e.g., human growth hormone (hGH), epidermal growth factor, insulinlike growth factor, platelet-derived growth factor, transforming growth factor, nerve growth factor, granulocyte colony stimulating factor, granulocyte macrophage colony stimulating factor, macrophage colony stimulating factor, or erythropoietin), an oncoprotein (e.g., ras, fos, jun, myc, kit, or myb), a tumor suppressor protein (e.g., p53), a milk protein (e.g., β casein or lactoferrin), a peptide hormone (e.g., insulin or follicle-stimulating hormone), a hormone receptor (e.g., an insulin receptor), a translation factor (e.g., eukaryotic initiation factor 4E), a transcription factor (e.g., mammary gland specific factor), protein C, al-antitrypsin, urokinase plasminogen activator, human serum albumin, cystic fibrosis transmembrane conductance regulator, gamma-interferon, human CD4, or erythropoietin. Where the heterologous protein or enzyme is of human origin, the heterologous protein or enzyme is particularly useful in the invention.

Where the heterologous gene product is an antisense oligonucleotide or a ribozyme, the targeted gene can be, without limitation, a β-lactoglobulin gene, an acetyl CoA carboxylase gene, a galactosyltransferase gene, or an α-lactalbumin gene.

Preferably, the genetic construct is treated to enhance its ability to cross the membrane of an epithelial cell. For example, the genetic construct can be treated so that it forms a complex with a lipid. Cationic, neutral, negatively-charged, and pH-sensitive lipids can be used. Useful cationic lipids include dioleyldimethylammonium chloride; 1,2-bis-oleoyloxy-3-trimethylammoniopropane; 1,2-dioleyl-3-N,N, N-trimethylaminopropane; dioleoylphosphatidylethanolamine; 3β[N-(N',N'-dimethylaminoethane)-carbamoyl] cholesterol hydrochloride; dimethyl dioctadecyl ammonium bromide, 2,3-dioleyloxy-N-[2(sperminecarboxamido)ethyl] -N,N-dimethyl-1-propanaminium tri-fluoroacetate; cholesterol; DL-1,2-dioleoyl-3-dimethylaminopropyl-β-hydroxyethylammonium; and DL-1,2-O-dioleyl-3-dimethylaminopropyl-β-hydroethylammonium. If desired, the genetic construct can be treated so that it forms a complex with a polycationic compound, such as poly-lysine or poly-ornithine. The genetic construct can be treated with one or more lipids or polycationic compounds. In addition, the genetic construct can be treated with a combination of a polycationic compound(s) and a lipid(s). These treatments can improve uptake and nuclear localization of the genetic construct.

Mammogenesis and lactogenesis can be hormonally induced in the mammal prior to infusion of the genetic construct. This treatment of the mammal can stimulate the mitotic index of the mammary gland, increasing the ability of the mammary epithelial cells to take up DNA. In addition, this treatment offers the advantage that milk containing the heterologous protein can be obtained from the mammal before the mammal naturally reaches sexual maturity. Also, the ruminant mammal can be treated to loosen the apical tight junctions of the epithelial cells of the cap, facilitating the flow of the genetic construct across the epithelium. For example, ethylene glycol bis (β-aminoethyl ether) N,N,N', N'-tetraacetic acid (EGTA) or ethylenediaminetetraacetic acid (EDTA) can be infused into the gland. In addition, certain agents (e.g., chloroquine and colchicine) can be employed to enhance the release of the complexed genetic construct.

By "signal peptide," is meant a polypeptide which facilitates secretion of the protein to which it is linked. The signal peptide can be naturally occurring in the heterologous protein (e.g., signal peptides of naturally secreted proteins such as human placental β-galactosidase, β-galactosidase of *Aspergillus niger*, and hGH). Alternatively, the genetic construct can be engineered so that a signal peptide is bonded to the heterologous protein.

By "liquid carrier," is meant any physiologically acceptable solution. Examples of suitable liquid carriers are water, 5% glucose, 5% sorbitol, 10% sucrose, OPTI-MEM™, phosphate buffered saline, and 10 mM Tris-HCl (pH 7.4).

By "infusion," is meant the introduction of a liquid complex into a cistern or duct through the streak canal.

By "ductal tree," is meant the branched network of tubular structures which conduct milk in a mammary gland.

By "streak canal," is meant the papillary duct at the lower end of the teat which leads to the ductal tree and which, typically in conjunction with a sphincter muscle, holds milk within the gland cistern between milkings.

By "sexual maturity," is meant the onset of the estrous cycle.

By "heterologous" protein, gene product, nucleic acid, or sequence, is meant a protein, gene product, nucleic acid, or sequence which is introduced into a ruminant mammary epithelial cell. For example, a human or bacterial protein or gene product is heterologous to a ruminant mammary epithelial cell. In addition, a protein or gene product that is not naturally present in a mammary epithelial cell of a ruminant, but which is naturally present in another cell of the ruminant (e.g., insulinlike growth factor, insulin, or follicle stimulating hormone), is heterologous to the mammary epithelial cell. Also included, is a protein or gene product that is naturally present in a ruminant mammary epithelial cell, but which is expressed from a genetic construct which is not naturally present in the mammary epithelial cell (e.g., milk proteins such as β-casein and lactoferrin expressed from a plasmid). Expression of such a protein or gene product from a genetic construct can elevate the level of the protein or gene product in the mammary epithelial cell and/or milk.

By "tethered" polypeptide, is meant that a portion of the polypeptide is affixed to a cell membrane.

By "antisense oligonucleotide," is meant a nucleic acid which is capable of binding to a second nucleic acid and inhibiting expression of a gene. The antisense oligonucleotide can inhibit DNA replication and/or translation of mRNA into protein.

By blood "clotting factor," is meant any of the various plasma components involved in the process of coagulating blood.

By "growth factor," is meant any of the various proteins which stimulates cell proliferation or differentiation.

By "oncoprotein," is meant any of the various polypeptides which can cause transformation of a cell in which it is expressed.

By "tumor suppressor" protein, is meant a protein which inhibits excessive cell proliferation or differentiation.

By "peptide hormone," is meant any of the various proteins which is formed in one organ or part of the body and carried in the blood to another organ or part and which can alter the functional activity or an organ.

By "milk" protein, is meant any of the various proteins (e.g., β-casein and lactoferrin) which is secreted by the ductal tree and alveolar cells of a mammary gland.

By "hormone receptor" is meant a structural protein located on a cell surface or within the cytoplasm of a cell which specifically binds a peptide or non-peptide chemical substance which is formed in one organ or part of the body and carried in the blood to another organ or part and which alters the functional activity of another organ.

By transcription or translation "factor" is meant any of the various polypeptides which modulate transcription (e.g., polymerases, repressor, and enhancers) or translation (e.g., elongation factors), respectively.

The invention provides a convenient and efficient method for directly transferring a gene(s) into the mammary gland of a ruminant mammal to produce a heterologous protein in the milk of the mammal. Thus, useful human therapeutic proteins (e.g., human growth hormone) and veterinary therapeutic proteins (e.g., IL-6) can be produced in milk. The invention also provides a convenient method for altering the characteristics of milk. For example, the invention can be used to change the protein, lipid, or carbohydrate content of the milk. Useful milk products, such as those having a reduced lactose content, can readily be produced. Production of the heterologous protein in a mammal facilitates post-translational modification of the protein and obviates expensive cell culture media used in in vitro methods of protein production.

In various embodiments of the invention, the transferred DNA is protected against degradation and the efficiency of gene transfer is increased by complexing the DNA with a polycationic compound.

The invention also offers the advantage that the heterologous protein can be produced in large quantities. In addition, where the β-galactosidase is derived from Aspergillus niger, the enzyme is particularly useful for hydrolyzing lactose at an acidic pH (at pH 3-4). Where the β-galactosidase is derived from Bacillus subtilis, for example, the β-galactosidase is particularly useful for hydrolyzing lactose at low temperatures because this enzyme retains approximately 10% of its activity at 10° C., thus allowing the protein to function at a temperature which inhibits the growth of contaminating bacteria. Accordingly, a sample of milk including this enzyme is particularly useful for reducing the lactose content of a second sample of milk by simply mixing the two milk samples together. Other milk samples containing enzymes which are functional at low temperatures are also suitable for modifying a second milk sample.

Where the heterologous enzyme is an aspartic protease, the milk is particularly useful for producing cheese. Such proteases decrease the time required for milk to be clotted by rennet. Aspartic proteases can also increase the yield of cheese. The expression of a bovine β-casein in milk can also improve cheese yields. In addition, the production of bovine β-casein or other heterologous proteins (e.g., lactoferrin or lysozyme) in milk can increase the nutritional value of the milk.

Because heterologous enzymes can be tethered to the mammary epithelial cell membrane, the invention also enables the production of modified milk, while decreasing the concern that such milk contains heterologous enzymes. Tethering enzymes to the mammary epithelial cell membrane also decreases the demand placed on the cell's synthetic machinery, since the enzyme can act on components of the milk without being secreted into the milk.

Other features and advantages of the invention will be apparent from the following description of the preferred embodiments thereof, and from the claims.

DETAILED DESCRIPTION

The drawings will first be briefly described.
Drawings

Abbreviations

The following abbreviations are used herein:
CEBA cholesterol-ester-β-alanine
CHOL cholesterol
DDAB dimethyl dioctadecyl ammonium bromide
DMEDA 3β[N-(N',N'-dimethylaminoethane)-carbamoyl] cholesterol hydrochloride
DODAC dioleyldimethylammonium chloride
DOPE dioleoylphosphatidylethanolamine
DORI DL-1,2-dioleoyl-3-dimethylaminopropyl-β-hydroxyethylammonium
DORIE DL-1,2-O-dioleyl-3-dimethylaminopropyl-β-hydroethylammonium
DOSPA 2,3-dioleyloxy-N-[2(sperminecarboxamido)ethyl]-N,N-dimethyl-1-propanaminium trifluoroacetate
DOTAP 1,2-bis-oleoyloxy-3-trimethylammoniopropane
DOTMA N-[1-(2,3-dioleyloxy)propyl]-n,n,n-trimethyl ammonium chloride
hGH human growth hormone
htPA human tissue plasminogen activator
L-PE L-lysinyl-phosphatidylethanolamine Before providing detailed examples of the invention, we now describe some of the parameters of the invention.

Genetic Constructs Numerous linear and circular (i.e., plasmids) genetic constructs are suitable for use in the invention. Important features of such genetic constructs include: (1) DNA encoding a useful heterologous protein, ribozyme, or antisense oligonucleotide; (2) a naturally-occurring or provided sequence encoding a signal polypeptide which directs secretion of the heterologous protein from the cell if secretion is desired, or a naturally-occurring or provided sequence encoding a membrane-associated polypeptide if tethering is desired; (3) a promoter or transcriptional initiation regulatory region, and (4) a transcription termination region. Conventional methods known to those skilled in molecular biology can be used to assemble functional genetic constructs.

Regulation of Gene Expression

The promoter or transcription initiation regulatory regions can be heterologous to the cell to be modified. Examples of useful promoters include the human cytomegalovirus (CMV) immediate early promoter, the Simian Virus 40 (SV40) early promoter, the Rous Sarcoma Virus (RSV) promoter, and the adenovirus major late promoter. Other useful promoters include those which naturally drive the expression of mammary-specific genes. For example, the αS1-casein promoters, αS2-casein promoters, β-casein promoters, κ-casein promoters, β-lactoglobulin promoters, whey acidic protein promoters, and α-lactalbumin promoters can be used. If desired, the promoter can be operably linked to one or more enhancer elements such that the enhancer element(s) increases transcription of the gene encoding the heterologous gene product. Useful enhancer elements include, without limitation, enhancer elements from CMV, SV40, and the RSV long terminal repeat. Expression of the heterologous gene can be constitutive or, if desired, inducible by an external stimulus. Examples of inducible promoters include the metallothionein gene promoter, promoters with steroid hormone-responsive elements, the mouse mammary tumor virus long terminal repeat, and heat shock promoters (e.g., hsp70). Methods for inducing these promoters are described in the literature. During hormonal induction of lactation, the use of corticosteroids (e.g., dexamethasone) induces transcription through the MMTV promoter. The addition of zinc or cadmium to the ruminant's feed or water will drive expression through the metallothionein promoter.

Preferably, the genetic construct (i.e., plasmid) also includes a transcription termination region. Useful termination regions include a polyadenylation signal and the 3'-end of the gene from which the promoter region of the genetic construct was derived. Other useful transcription termination regions include termination regions which are known to affect mRNA stability, such as those derived from the bovine growth hormone gene, globin genes, or the SV40 early region.

Optionally, the linear or circular genetic construct includes an intron which can increase the level of expression of the heterologous gene. Generally, the intron should be placed between the transcription initiation site and the translational start codon; 3' of the translational stop codon; or within the coding region of the gene encoding the heterologous protein. The intron should include a 5' splice site (i.e., a donor site), a 3' splice site (i.e., an acceptor site), and preferably includes at least 100 nucleotides between the two sites. Particularly useful introns are those which are naturally found in genes of ruminants (e.g., genes encoding caseins).

If the genetic construct is circular, it preferably carries DNA sequences which facilitate its propagation in a eukaryotic or prokaryotic cell used to test the genetic construct. For example, the genetic construct can include an origin of replication suitable for maintaining the construct in a bacterium (e.g., E. coli). The construct can also include a selectable marker such as an ampicillin resistance gene or a neomycin resistance gene, or an amplification system (e.g., a dihydrofolate reductase gene). In addition, the genetic construct can carry sequences (e.g., inverted terminal repeat sequences) which enhance the rate at which the genetic construct is integrated into the chromosomal DNA of a cell. The genetic construct can also include sequences (e.g., EBNA-1 from Epstein-Barr virus) that allow for autonomous replication of the genetic construct in a cell.

Heterologous Gene Products

Practically any heterologous protein can be produced according to the invention. Particularly useful heterologous proteins include those which are of therapeutic value to humans or animals (e.g., htPA, hGH, and IL-6). Other particularly useful proteins include those which increase the nutritional value of the milk (e.g., β-casein and lactoferrin). Many genes encoding these and other useful proteins have been identified and cloned, allowing them to be readily subcloned for use in the invention.

Other particularly useful heterologous proteins include those which are valuable in food science. Among the useful proteins are those which possess an enzymatic activity directed toward a component of milk; such enzymes can be used to alter the lipid, protein, or carbohydrate content of the milk. For example, β-galactosidase can be produced with the invention to produce milk with a reduced lactose level. Genes encoding β-galactosidase can be derived from any of a number of organisms, including Aspergillus niger, (Kumar et al., 1992, Bio/technology 10:82); Bacillus stearothermophilus (U.S. Pat. No. 4,861,718); Escherichia coli (Kalnins et al., 1983, EMBO J. 2:593); Homo sapiens (Oshima et al., 1988, Biochem. Biophys. Res. Comm. 157:238); Kluyveromyces lactis (U.S. Pat. No. 5,047,340; Sreekrishna and Dickson, 1985, Proc. Natl. Acad. Sci. 82:7909; and Poch et al., 1992, Gene 118:55); Lactobacillus bulgaricus (Schmidt et al., 1989, J. Bacteriology 171:625); Streptococcus thermophilus (Schroeder et al., 1991, J. Gen. Microbiology 137:369); Streptomyces lividans (Eckhardt et al., 1987, J. Bacteriology 169:4249); or Sulfolobus solfataricus (Cannio et al., 1994, Biotech. Appl. Biochem. 19:233).

If desired, the gene encoding the heterologous protein can be mutated. Particularly useful mutations include mutations in the 5'- or 3'- untranslated regions of the gene, because such mutations may improve expression of the gene encoding the heterologous protein. Other useful mutations or deletions are those which increase secretion of the protein from the cell or inhibit retention of the protein inside the cell. For example, sequences encoding endoplasmic reticulum retention signals or other sorting inhibitory signals are preferably deleted from the genetic construct or mutated to be non-functional. In addition, truncated versions of naturally-occurring proteins can be used in the invention, provided that the truncated protein possesses a useful biological activity.

Each heterologous protein produced according to the invention should be bonded to a signal peptide if the protein is to be secreted from the mammary epithelial cell. The signal peptide can be a naturally-occurring component of the heterologous protein (e.g., the signal peptide of human placental β-galactosidase). Where the heterologous protein is not naturally a secreted protein, if secretion is desired, the genetic construct should be assembled such that a signal peptide is bonded to the heterologous protein so that the signal peptide directs secretion of the protein from the cell. Useful signal peptides can be derived from genes such as casein genes, the gene for human alkaline phosphatase, or the gene for melittin.

Tethered Enzymes

Where the genetic construct encodes an enzyme to be tethered to the epithelial cell membrane, the genetic construct can include a sequence encoding a membrane-associated polypeptide. For example, the genetic construct can include a sequence derived from β-1,4-galactosyltransferase (see, e.g., Masri et al., 1988, Biochem. Biophys. Res. Comm. 175:657-663), lactase-phlorizin hydrolase (see, e.g., Mantei et al., 1988, EMBO J.

7:2705–2713), the thy-1 protein (see, e.g., Brown et al., 1989, Science, 245:1499–1501), or the sodium/glucose transporter (see e.g., Kong et al., 1993, FEBS Letters 333:1–4).

Tethering an enzyme to the cell membrane allows the enzyme to be active on a component of milk, while inhibiting secretion of the enzyme into milk obtained from the mammal. Tethering the enzyme to the cell membrane can decrease the amount of heterologous enzyme that must be synthesized for modification of the milk components. While secreted enzymes remain in contact with milk in the bovine duct for approximately 12 hours before they are removed with the milk, the timespan for tethered enzymes is limited only by the natural turnover of the epithelial cell membrane. Because the enzyme remains in the duct where it can act on milk produced over a long period of time, the cell may not need to synthesize as much of the heterologous enzyme as would be required if the heterologous enzyme were secreted. In addition, while milk obtained from such mammals can be modified as desired (e.g., to have a reduced lactose content), tethering the enzyme to the cell membrane decreases the concern that the modified milk contains an undesired heterologous enzyme.

Antisense Oligonucleotides

Where the genetic construct encodes an antisense oligonucleotide for inhibiting gene expression, the construct is engineered to produce an oligonucleotide which hybridizes to DNA or mRNA of the gene. Generally, this aspect of the invention can be practiced using art-known antisense strategies. The DNA sequences of a number of mammary epithelial cell genes are known. Appropriate targets include, without limitation, genes encoding a β-lactoglobulin (see e.g., Ivanov et al., 1988; J. Biol. Chem. 369:425–429, and Silva et al., 1990, Nucleic Acid Res. 18:3015), an acetyl CoA carboxylase, a galactosyltransferase (Shaper et al., 1986, Proc. Natl. Acad. Sci. 83: 1573–1577; Masibay et al., 1989, Proc. Natl. Acad. Sci. 86: 5733–5737; Masri et al., 1988, Biochem. Biophys. Res. Comm. 175:657–663), and an a-lactalbumin (Vilotte et al., 1987, Biochimie 69:609–620). Thus, those skilled in molecular biology will be able to design a genetic construct encoding an antisense oligonucleotide of a suitable sequence and length. Preferably, the antisense oligonucleotide is between 2 and 1,000 nucleotides in length.

Ribozymes

The gene transfer method of the invention can also be used to deliver genetic constructs encoding ribozymes to the mammary epithelial cells. Conventional strategies can be used in the design of genetic constructs encoding ribozymes. Appropriate target nucleic acids include, without limitation, those which encode β-lactoglobulin, acetyl CoA carboxylase, galactosyltransferase, and α-lactalbumin.

Isolation and Characterization of Genetic Constructs

The genetic constructs useful in the invention can be prepared using conventional techniques for DNA isolation. If desired, DNA quality can be assessed with standard methods, such as measuring optical density or analyzing the DNA by electrophoresis. Preferably, the DNA is endotoxin free, and suitable methods include those which have been approved for purifying DNA for use in humans (e.g., the use of a Qiagen DNA extraction kit followed by the use of an endotoxin elimination kit). If desired, the genetic constructs can be further characterized by sequencing the DNA molecules, particularly at junctions formed by the ligation of two DNA molecules. The creation of partial restriction maps from the genetic constructs can provide information regarding the orientation of the gene encoding the heterologous protein relative to the other components of the construct.

Enhancement of Uptake of a Genetic Construct by a Cell

If desired, the mammary secretory epithelium can be treated to increase the ability of a cell to take up a genetic construct. Preferred treatments include the infusion of EGTA, EDTA, chloroquine, and/or colchicine 24 to 48 hours prior to infusion of the genetic construct. Treatment with EDTA or EGTA loosens the apical tight junctions and lowers the resistance across the mammary secretory epithelium, facilitating transfer of molecules from the duct to the cap. Generally, an EDTA or EGTA concentration of 10 to 100 mM is suitable for increasing the uptake of a genetic construct by a mammary epithelial cell. If desired, traces of EDTA or EGTA can be removed by infusion of phosphate-buffered saline in a volume which produces a visible swelling of the gland (approximately 1–5 ml). Enhanced expression of the heterologous gene product may be achieved by treating the ruminant with a combination of colchicine (0.1–10 µg/quarter) and chloroquine (5–100 gg/quarter). The preferred volume of the solution employed for infusion of a solution of EDTA, EGTA, colchicine and/or chloroquine is dependent upon the age of the mammal and the size of the mammary gland. If the solution is infused in a suitable volume, a visible swelling of the gland can be observed upon infusion. Generally, a volume of 2–30 ml can be used; preferably, the volume is 3–15 ml for animals of 2–6 months of age.

A variety of transfection systems can be employed to enhance delivery of genetic constructs into mammary epithelial cells in vivo and in vitro. Useful lipids include DMEDA, CHOL, DDAB, DMEDA, DODAC, DOPE, DORI, DORIE, DOSPA, DOTAP, DOTMA, LIPOFECTAMINE™ (3:1 (w/w) DOSPA: DOPE) LIPOFECTIN™ (1:1 (w/w) DOTMA:DOPE), DODAC:DOPE (1:1), CHOL:DOPE (1:1), and other combinations of the lipids in appropriate ratios, as determined by the ability of the lipid(s) to help transfer a genetic construct into a cell (see, e.g., W093/03709). The lipids which are useful in the invention can be formulated in a variety of methods. In a preferred method, each lipid (e.g., DDAB, DODAC, or DOPE) is suspended in $CHCl_3$, the lipids then are mixed together at the desired ratios for combinations of lipids (e.g., DODAC:DOPE (1:1)), the solvent is removed under vacuum, and the lipid mixture is hydrated in sterile distilled water or 5% dextrose by vortexing the lipid sample. The resulting multilamellar vesicle suspension is freeze/thawed with cycles of liquid nitrogen and warm water, and the lipids then are extruded through 100 nm filters.

The genetic construct/lipid complexes can be prepared in the absence of serum and antibiotics and in a small volume (i.e., 1.0–2.0 ml total). Generally, it is preferred that the genetic construct and lipid be mixed in a polystyrene tube, since lipids can stick to certain types of tubes, resulting in loss of the lipids. A suitable volume for preparing the genetic construct/lipid complex prevents precipitation of the DNA; this volume can be empirically determined for each lipid. Generally, the volume should be sufficiently large that the DNA concentration does not exceed 300 µg/ml and the lipid concentration does not exceed 1,500 µg/ml. Preferably, the DNA concentration is 100 to 200 µg/ml; preferably, the lipid concentration is 500 to 1,000 µg/ml. The DNA/lipid complex can be prepared by mixing a low ionic strength solution of the genetic construct at a 1:1 ratio with a low ionic strength solution of the desired lipid. For example, a 0.5 ml sample of DNA in water can be mixed with a 0.5 ml solution of lipid. The lipid to DNA charge ratio will vary and depend on the lipid selected for use. Preferably, the ratio of positive to negative charges is from 0.25:1 to 4.0:1 (lipid:DNA), inclusive; more preferably, the ratio is from 0.5:1 to 2.0:1 (lipid:DNA), inclusive. For example, the optimal lipid:DNA charge ratio where the lipid is a combination of DODAC and DOPE is from 0.5 to 1.5 (lipid:DNA), inclusive. Although DNA/lipid complexes begin to form immediately after the DNA and lipid solutions are mixed, it is preferable to allow the mixture to incubate for 30 to 60 minutes at room temperature before increasing the volume to the infusion volume. Longer incubations are also acceptable, since the complexes are very stable. Where the liquid complex is formed with a polycationic compound, the DNA and polycation preferably are mixed at molar ratios ranging from 3:1 to 10:1 (polycation:DNA).

Optional Assay of a Genetic Construct in a Cultured Cell

If desired, the usefulness of a genetic construct can be estimated by introducing it into a cultured mammary epithelial cell line in vitro and assaying for production of the desired secreted protein, tethered enzyme, antisense oligonucleotide, or ribozyme. A particularly useful cell line for testing genetic constructs is the bovine mammary epithelial cell line termed MAC-T (U.S. Pat. No. 5,227,301, incorporated herein by reference). MAC-T cells display several features of differentiated mammary epithelia. For example, these cells feature apical microvilli and apical junctional complexes, imparting on the cells an apical-basal polarity. In addition, they form high resistance monolayers. In the presence of extracellular matrix and lactogenic hormones, MAC-T cells differentiate and secrete endogenous, mammary-specific proteins. If desired, MAC-T cells can be used for testing genetic constructs to be introduced into any of the ruminants, including constructs to be introduced into sheep and goats. Thus, these cells provide an art-recognized model system for ruminant mammary glands.

MAC-T cells can be cultivated on tissue culture plastic in standard cell culture media. For example, complete media composed of Dulbecco's Modified Eagle's medium (DMEM) supplemented with 10% fetal bovine serum (FBS), 5 µg/ml insulin, 1 µg/ml hydrocortisone, 1–5 µg/ml prolactin, and 50 µg/ml gentamycin incubated in 5% carbon dioxide, water-saturated atmosphere at 37° C. provides suitable growth conditions for the cell line (Huynh et al., 1991, Exp. Cell Res. 197:191–199). One day prior to transfection, the MAC-T cells can be treated with trypsin and plated at the desired density; a density of 1 to $1.5 \times 10^5$ cells/35 mm dish is suitable.

Infusion

Prior to infusing the genetic construct (with or without a polycationic compound) into a mammal or testing it in a cultured cell, the genetic construct is mixed with an liquid carrier to form a liquid complex. Isotonic liquid carriers such as 5% dextrose, PBS, and cell culture media, such as OPTI-MEM™ are particularly useful. The liquid carrier can be used to adjust the volume of the solution of the genetic construct to a volume that is appropriate for infusion into the ductal tree of a mammal or for adding the DNA/lipid complex to cultured cells for preliminary testing.

For transferring genetic constructs in liquid complexes into cultured mammary epithelial cells, the liquid complex will generally be added to the culture dish in a volume of 0.5–1.5 ml, carrying a total of 1 to 2 Ag of DNA per 35 mm dish. The DNA/lipid mixture can be allowed to incubate with the cultured cells (typically, 4 to 16 hours is sufficient) before replacing the cell culture media and assaying for gene expression.

For infusion of liquid complexes carrying genetic constructs into a mammary gland, the optimal volume of the DNA infusion complex will vary with the age of the mammal and the size of the mammary gland, with the desired volume producing a visible swelling of the infused quarter. Generally, a volume of approximately 2 ml for a 1 month old heifer up to a volume of approximately 15 ml for a 6 month old heifer is sufficient. Appropriate volumes for sheep and goats are also based on a visible swelling of the gland. Typically, the total amount of genetic construct introduced into a heifer is 100 µg to 2.0 mg per quarter; preferably, the amount is 500 µg to 1 mg per quarter. In sheep and goats of 1–6 months of age, the mammary gland is smaller in size than it is in heifers, and the number of epithelial cells is smaller. For sheep and goats, the preferred amount of DNA infused is 300 to 800 µg per half.

Liquid complexes can be infused through the streak canal with the aid of a cannula, syringe and needle according to conventional infusion method (Quiroga, et al., 1993, Am. J. Vet. Res. 54:1984). If desired, an anesthetic can be used during the infusion process. If the gland cistern is large, a balloon catheter can be inserted into the mammary cistern of the mammal, allowing a smaller volume of infusant to be used. Because the quarters of the mammary gland are distinct, one of the quarters of the mammary gland can be used as a control by infusing it with a liquid carrier which lacks a genetic construct. Massaging the mammary gland after infusion of the genetic constructs helps ensure that the genetic constructs are evenly distributed and that they contact the targeted epithelial cells.

Expression Assays

A variety of art-known methods can be used to assay for proper gene expression, if desired. For example, secretion of the heterologous protein by cultured epithelial cells can be measured by assaying cell culture supernatants (e.g., by SDS-PAGE, Western blot, ELISA, or enzyme activity assays (e.g., assays employing substrates of β-galactosidase)). Similarly, intracellular production of the heterologous protein can be measured by assaying cell extracts. For tethered proteins produced on the cell surface, FACS analysis of the cells can be useful in assaying for expression of the heterologous protein. In addition, techniques such as SDS-PAGE, Western blotting, immunofluorescence, and ELISAs are useful for detecting tethered proteins. A number of methods are suitable for assaying for production of antisense oligonucleotides and ribozymes. For example, probes specific for the antisense oligonucleotide or ribozyme can be designed and used in assays such as Northern blot analysis, slot/dot blot hybridizations, RNase protection analysis, and RT-PCR analysis. In addition, an assay of the level of the protein encoded by the targeted gene, with any of the techniques described above, can be employed. A decrease in the protein level is indicative of proper expression of the heterologous antisense oligonucleotide or ribozyme.

Raising the Mammal

Conventional methods can be used to raise the mammal and obtain milk from the mammal.

Detection of Heterologous Gene Products in Mammary Glands and Milk

If desired, the mammary gland or milk can be analyzed for expression of the heterologous gene product after infusion of the liquid complex carrying the genetic construct. Generally, 48 hours is sufficient to allow uptake of the genetic construct and expression of the heterologous gene product. After euthanizing the mammal, the mammary gland can be dissected and analyzed using standard methods for detecting expression of a gene (e.g., immunofluorescence, western blotting, and RNA hybridization assays). If desired, the lactating animal can be biopsied, and the tissue can be analyzed with standard methods. Milk obtained from the mammals by induced or natural lactation can also be analyzed with the use of commonly-known methods for protein detection (e.g., ELISA, Western blotting, or enzyme activity assays). Where the heterologous gene product affects the level of lactose in the milk of the mammal, conventional methods can be used to measure the lactose content of the milk (see, e.g., H. 0. Beutler, 1984, Methods of Enzymatic Analysis (H. 0. Bergmeyer, ed.) 3rd ed. vol. VI, pgs. 104-112, Verlag Chemie, Weinheim, Basel and Essig and Kleyn, 1983, J. Assoc. Off. Anal. Chem. 66:1514–1516). If desired, the milk can be treated (e.g., by centrifugation) to reduce the fat content of the milk prior to analysis.

There now follow detailed examples of the invention.

Example I.

Direct In Vivo Gene Transfer of CMV-Lac Z Vectors into the Mammary Glands of Young Heifers Recombinant DNA procedures: A genetic construct termed CMV-Lac Z (Clontech) was used to express β-galactosidase in the mammary glands of heifers. This plasmid has an RNA splice site, a polyadenylation signal, and the full-length E. coli β-galactosidase gene.

Lipid Carrier-Plasmid Liquid Complexes: The plasmid DNA was diluted in sterile water to a concentration of 1 μg/μl. Lipid preparations employed LIPOFECTIN™ (1 mg/ml) or LIPOFECTAMINE™ (1 mg/ml). The ratio of plasmid DNA to cationic lipids which provided the maximum transfection efficiency was first determined in vitro using the MAC-T mammary epithelial cell line. A 1:6 ratio of DNA:lipid (LIPOFECTAMINE™ or LIPOFECTINT, (w:w) 1.7 jig: 10lig in a 35 mm dish) produced maximum transfection efficiencies of 20% (with LIPOFECTAMINE™). This ratio of DNA:lipid was subsequently used for the genetic construct infused into a mammal.

The plasmid DNA (50 μg or 150 μg) was suspended in 0.5 ml of OPTI-MEM™ (GIBCO/BRL). Complex formation progressed for a maximum of 30 minutes at room temperature with 300 μg to 900 μg of lipid suspended in 0.5 ml of OPTI-MEM™ in a sterile polystyrene tube. The volume of infusant which was used depended on the age and size of the mammary gland to be infused. The infusant was adjusted with OPTI-MEM™ to a volume of 2–3, 4–5, 7–8, or 10–13 ml for mammals that were 2, 3, 4, and 5 months of age, respectively. Complexes were prepared no more than 30 minutes before being infused into the mammal. The complexes were infused into three of the quarters of the mammary gland through the streak canal with the aid of a sterile syringe and an 18- or 23-gauge needle. The fourth quarter served as a control and received OPTI-MEM™ alone. The volume of solution injected into a quarter of the gland was empirically determined on the basis of the size of the gland. A visible swelling of the infused quarter was used as the criterion for the correct volume being infused. Following infusion, each quarter of the mammary gland was massaged for at least 5 minutes to ensure that the infusant was distributed to the target cells. In certain instances the gland received one, two, or four DNA/lipid infusions. Twenty-four hours prior to DNA infusion, the glands were infused with 30–70 mM EDTA or OPTI-MEM™. Before infusion of the DNA, each quarter received 2–4 ml of phosphate-buffered saline in order to remove traces of EDTA or EGTA.

As a control, an aliquot of the DNA/lipid complex used for infusion was tested for its ability to transfect MAC-T cells. These transfections were performed as described above.

Tissue Sampling: Forty-eight hours after infusion, the animals were euthanized, and the udder was dissected from the carcass. The mammary gland then was bisected at the suspensory ligament. At this stage (2 months) of development, the gland was primarily a fat pad with small (3 cm in diameter) spheres of glandular tissue located proximal to the teat. Each quarter was cross-sectioned using a surgical blade, cutting from the center of the teat and down through the center of the gland. Samples (1 cm$^3$) were taken from each half of the quarter and fixed in either 10% formalin solution or in Bouins' solution for 24 to 72 hours. The fixed mammary tissue was then processed for light microscopy using standard histological techniques. Briefly, the samples were dehydrated in a series of alcohol solutions, embedded in paraffin, and sectioned to a thickness of 3 μm. Some of the sections were stained with hematoxylin and eosin in order to observe the overall architecture of the tissue.

Primary Cell Analysis: A portion of the biopsied mammary gland tissue was used to provide epithelial cells for in vitro analysis. Biopsy samples were trimmed of visible fat and connective tissue, then minced with sterile blades. The tissue was dissociated for 2 hours at 37° C. with shaking (~200 rpm), fluted dissociation flasks containing dissociation media [HEPES (300 mM), glucose (12.2 mM), Collagenase I and II (203 IU), hyaluronidase (25 IU), pronase (0.01% w/v), bovine serum albumin (1 mg/ml), gentamycin (50 μg/ml), penicillin G (10,000 IU/ml), streptomycin sulphate (10,000 μg/ml), and amphotericin B (250 ng/ml)].

Released cells and clumps were then filtered through a 100-mesh nylon filter into primary cell media and centrifuged for 15 minutes at 800×g. Pelleted cells were resuspended in primary cell media (DMEM:M199; 50:50, buffered with 0.9 g of NaHCO$_3$, antibiotics identical to those used in the dissociation medium, bovine insulin (10 μg/ml), hydrocortisone (1 μg/ml) and 10% FCS). The cells then were plated in 35 mm dishes. The remainder of the mammary gland biopsy was frozen at −70° C. and used for DNA analysis (i.e., PCR analysis) and protein extraction.

Detection of the CMV-Lac Z DNA Construct by PCR Analysis: The heterologous Lac Z gene in the mammary glands and cultured cells (derived from glands infused with the CMV-Lac Z construct) was detected with PCR technology. Genomic DNA samples were isolated from mammary biopsy tissue and cultured cells for use as templates in PCR reactions using CMV-Lac Z construct-specific primers. PCR was performed in a total volume of 50 μl, containing 200 ng of mammary gland or primary culture cell DNA, 2.5 μM of each of the CMV-Lac Z construct-specific primers, 200 μM of each of the dNTPs, 1.5 MM MgCl$_2$, and 0. 13 units of TaqI polymerase. The sequences of the primers used to amplify a 560 bp fragment from CMV-Lac Z were as follows:

ACB02 (pos. 841–860 bp) 5'-AAAGAGCCTGCTAAACGAAA-3' ACB03 (pos. 1381–1401 bp) 5'-CAGATGAAACGCCGAGTTAA-3'

The PCR reactions included a denaturation step at 94° C. for 5 minutes and an incubation at 60° C. for 5 minutes, followed by 30 amplification cycles. Each cycle was carried out for 1 minute at 94° C., 1 minute at 60° C., and 2.5 minutes at 72° C. The amplification products were then analyzed on 1.5% agarose gels. An additional set of primers, specific for the endogenous bovine αS1-casein gene (amplifying a 370 bp fragment), were used in the same PCR reactions as a positive PCR control. The sequence of the casein specific primers a re as follows:

ACB12 5'-TTACCTGTCTTGTGGCTGTTGCT-3' ACB13 5 '-TGGACCCAGGCAAAGAGACTAG-3'

Expression of Lac Z in Dissociated Primary Bovine Mammary Gland Cell Cultures: Primary cell cultures derived from mammary glands infused with DNA/lipid liquid complexes were harvested after trypsin treatment after four, six, or eight days in culture after infusion. The cell cultures were used for analysis by PCR, immunofluorescence. Genomic DNA was extracted according to standard procedures.

The immunofluorescence analysis was carried out as follows. The cells were washed twice in PBS containing 0.05% Tween-20 (PBS-T), fixed in methanol for 10 minutes at 4° C., and rinsed twice with PBS-T. Next, the primary antibody, anti-$E.$ $coli$ β-galactosidase (2 mg/ml), diluted 1:500 in PBS/3% BSA/1:100 goat serum, was added to the cells and incubated at room temperature for 1 hour. Following at least three washes with PBS-T, the second antibody, a goat anti-mouse FITC, was applied to the cells at a 1:100 dilution in PBS/3% BSA/1:100 goat serum, and incubated for 1 hour at room temperature. The cells were rinsed four times with PBS-T, permanently mounted using glycerol, and observed using standard immunofluorescence techniques.

Expression of β-galactosidase in Tissue Sections

Detection by Immunofluorescence: Biopsied mammary gland tissues were fixed in either 10% formalin or Bouins' solution, embedded in paraffin, sectioned to a thickness of 3–5 μm, and collected on coated glass slides. Prior to removing the paraffin with xylene, the slides were incubated at 50° C. for 15 minutes. The tissue sections were rehydrated by sequentially passing them through graded alcohols, distilled water, and PBS. The sections then were fixed for 10 minutes in methanol, washed twice in PBS-T, and blocked with a solution of 3% BSA and 10% sheep serum in PBS. The tissue samples were incubated with the primary and secondary antibodies and washed as described above for cell immunofluorescence.

Detection by Streptavidin: Tissue sections were de-paraffinized and dehydrated as described above. After the final alcohol bath, tissue sections were rinsed for 5 minutes in water and 10 minutes in Tris-HCl buffer (100 mM, pH 7.6), then covered with 10% heat-inactivated normal goat serum. The primary antibody was the same as that described above. All subsequent procedures were according to the conventional methods for detection with streptavidin. Color development was performed using a HistoMark X-GAL substrate set (Kirkegaard & Perry Inc., Md.), and sections were examined using conventional light microscopy techniques.

Results: PCR analysis of tissues biopsied from 9 animals at 2, 3, or 4 days after infusion with liquid complexes carrying either CMV-Lac Z DNA/lipid complexes or DNA alone produced a band of the expected size, indicating that DNA persisted in the mammary gland cells for several days. In order to confirm that the detected DNA was from the nuclei of transduced cells, cultures of cells derived from the same tissue biopsies were analyzed by PCR after 3, 6, or 9 days in culture. Of 35 biopsies-primary cultures analyzed, only the quarters that received DNA/lipid were positive in the PCR analysis. Primary cultures from quarters receiving DNA alone did not produce any visible product during the PCR (sensitivity was at 500 copies). In addition, the data indicated that the DNA persisted in the cells for at least 9 days after infusion.

Results obtained by immunofluorescence analysis of tissue sections assayed for the presence of the Lac Z product correlated with the data obtained by PCR analysis. Cells lining the ducts were immunoreactive with antibodies directed against β-galactosidase, strongly indicating successful gene transfer.

We can conclude from these experiments the following:
(1) LIPOFECTAMINE™ was more efficient in transferring DNA than was LIPOFECTIN™, however, both of the lipids are useful; and (2) the EGTA treatment increased the efficiency with which DNA was transferred into cells. The differences in efficiencies between treatments was determined by PCR-based assays of DNA copy numbers.

Example II.

Secretion of Human Growth Hormone by the Bovine Mammary Gland

This example illustrates that human growth hormone can be produced in the milk of dairy cattle.

Figure 1:
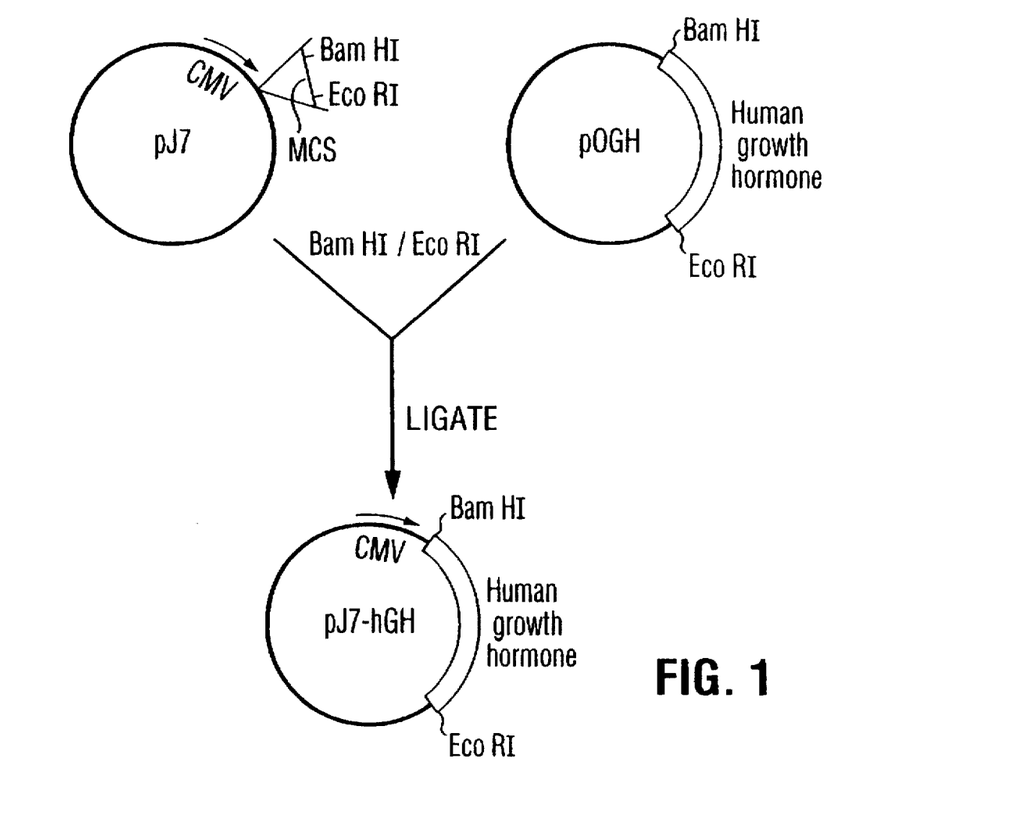
FIG. 1 is a schematic representation of the construction of pJ7-hGH.

Recombinant DNA Procedures: Plasmid POGH (from Dr. E. Cohen, University of Montreal) includes a 2.156 Kb BamHI/EcoRI genomic fragment which encodes human growth hormone. The 2.156 Kb fragment was removed from plasmid POGH by digestion with BanlHI and EcoRI, purified, and ligated directly into the BamHI and EcoRI sites of pJ7 (from Dr. G. Matlashewski, McGill University, Montreal). Plasmid pJ7 carries the cytomegalovirus (CMV) early promoter (FIG. 1). The plasmid resulting from cloning the human growth hormone gene into pJ7 was termed pJ7-hGH.

To confirm the plasmid's functionality, pJ7-hGH was transfected into MAC-T cells using the lipofection method described above, and media from the transfected cells was harvested 48 hours after lipofection. The concentration of hGH in the media was measured by ELISA.

Infusion: For infusion, a cannula was non-surgically inserted into the streak canal of young heifers to dilate it and thereby allow the introduction of material into the mammary ductal tree. The infusion of DNA can be achieved with commonly-used veterinary procedures for the administration of intramammary antibiotics. Heifers were fasted for 12 hours, but given water, prior to the infusion in order to reduce the incidence of regurgitation. Animals were anesthetized with XYLAZINE™ HCl ($C_{12}H_{16}NS \cdot HCl$) administered at a dosage of 0.4 to 0.9 mg/kg body weight; this dosage provides lateral recumbency for 30 minutes. The udder area was then washed, sequentially, with soapy water, 70% ethanol, and LODOVET™ (1% iodine solution). The liquid carrier was sterile 5% dextrose or OPTI-MEM™. A total of 2–15 ml of liquid carrier, including 150–600 μg of the genetic construct, was infused into each experimental quarter of the mammal's mammary gland. A round-ended 22-gauge needle was used to dilate the sphincter muscles at the teat end. When the cannula was removed, the sphincter muscles were competent and prevented the loss of infusate from the mammary gland. The mammary gland then was massaged to facilitate distribution of the infusate.

Hormonal Induction of Lactation in Young Heifers: Methods for hormonal induction of mammogenesis and lactation have been developed for sexually mature dairy cattle (Smith et al., 1974, J. Dairy Sci. 57:296), sexually mature goats (Fowler et al., 1991, J. Dairy Sci. 58:151), and sexually mature sheep (Fulkerson and McDowell, 1974, J. Endocrinol. 63:167–174). One procedure involves a 20-day schedule of injections, including 7 days of estrogen (0.1 mg/kg body weight/day) and progesterone (0.25 mg/kg body weight/day) given in two doses spaced 12 hours apart, followed by three intramuscular injections of reserpine (4 mg/day) on days 11, 13, and 15, followed by two intramuscular injections of dexamethazone (20 mg/day) on days 19 and 20. If desired, the reserpine injections can be omitted.

We have found that the procedures for stimulating mammogenesis and lactogenesis in sexually mature ruminants can be applied to non-sexually mature (i.e., prepubertal) heifers of approximately 3 months of age and older. Hormonal induction allows for the presence of the heterologous gene product to be assayed at an age of the mammal earlier than naturally-occurring sexual maturity. We applied estrogen and progesterone as described above, followed by the three dexamethazone injections at days 8, 9, and 10. Reserpine was not used, although it may be used, if desired. Animals subjected to the hormonal treatment described above also received two DNA/lipid infusions at days 5 or 6 and at day 7 of the estrogen/progesterone treatment. DNA was prepared as described above, and the complexes were formed in a final volume of 10 ml OPTI-MEM™. The hGH expression vectors (150 µg) complexed with lipids were infused into a quarter of the mammary glands of three 5 month and three 6 month old heifers. In total, 300 µg of the pJ7-hGH construct complexed with 1.8 mg of LIPOFECTAMINE™ was infused into each animal.

Milk from animals that had been hormonally induced and infused with the hGH DNA/lipid formulations was removed from the animals by hand milking, and the fat was removed by centrifugation of the milk. The resulting skim milk was stored frozen at −70° C. until it was assayed.

The hGH concentration in the milk was assayed as follows. Three 100 µl aliquots of skim milk were added, separately, to wells of a microtiter plate with a solid-phase coupled antibody (mouse anti-hGH). The samples were then incubated with gentle mixing for 30 minutes at room temperature. The wells were then washed, and 100 µl of anti-hGH antibody conjugated to horse radish peroxidase was added to each well, followed by incubation as described above. The wells were again washed, and the plate was developed with an enzyme substrate solution for 15 minutes before the reaction was stopped. The optical density at 414 nm was then measured with a kinetic microplate reader. A standard curve was established with various concentrations of hGH. The addition of up to 10 mg of bovine growth hormone indicated the bovine growth hormone does not interfere with this assay. This assay system was linear from 0 to 10 ng/ml, and the sensitivity of the assay was 0.05 ng/ml.

Milk was also analyzed for the presence of hGH by Western blot analysis. The bovine milk was diluted 1:6 with distilled water, defatted by a brief centrifugation, and the caseins were precipitated by addition of either an equal volume of 100 mM sodium acetate or by addition of 1N HCl to a final pH of 4.6. After a 10 minute centrifugation (8,000×g), the whey fraction was removed and precipitated with trichloroacetic acid (added to a final concentration of 10%). The proteins were then recovered by centrifugation, separated by SDS-PAGE, transferred onto nitrocellulose membrane, and probed with an anti-hGH monoclonal Ab (1:1000) Immunoreactive bands were visualized using an enhanced chemiluminescent (ECL) system (Amersham); immunoreactive bands can be detected with other conventional methods as well.

Results: Our results indicate that the use of a pJ7-hGH expression vector was an effective means for producing hGH within mammary cells in culture and within the mammary gland in vivo. Transiently transfected MAC-T cells routinely produced 7–10 ng/ml per 48 hours per $2\times10^5$ cells. Non-transfected MAC-T cells did not produce detectable levels of hGH. These in vitro data demonstrated that the pJ7-hGH expression vector was correctly constructed and that it could direct the secretion of human growth hormone from bovine mammary epithelial cells.

Figure 2:
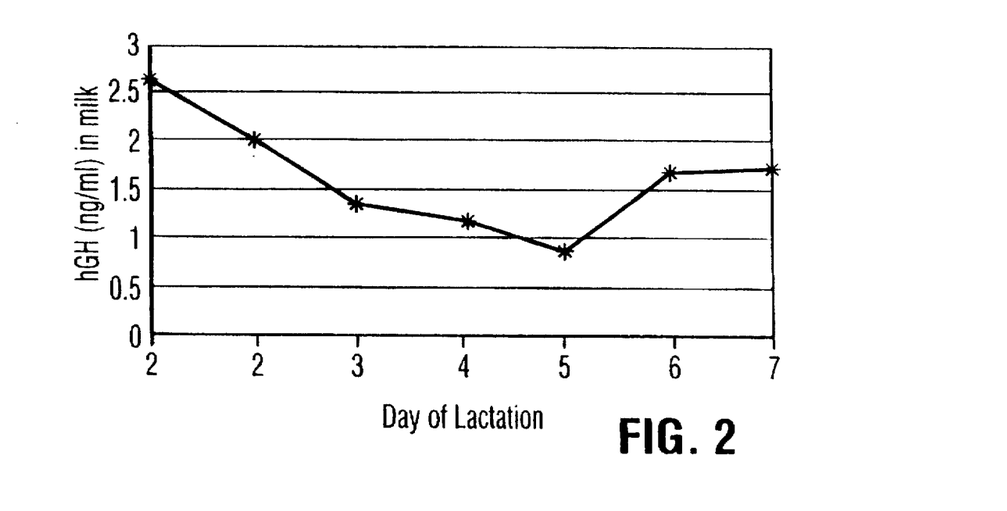
FIG. 2 is a plot of the hGH concentration in milk versus the day of lactation.

Of the six animals used in this example, three responded to the hormonal treatment and produced milk (174–9,000 ml) which persisted from 4 to 17 days. Milk produced in one of the three animals that were induced to lactate and infused with the hGH DNA/lipid complexes (the animal of 5 months of age) contained hGH at the levels shown in FIG. 2.

Example III.

In another series of experiments, DODAC:DOPE (1:1) lipid was used. A direct comparison of the transfection efficiencies between DODAC:DOPE (1:1) and LIPOFECTAMINE™ was performed using the CMV-Lac Z construct and MAC-T cells.

The tested lipid:DNA ratios are shown in Table 1. The DNA/lipid complexes were allowed to interact with the MAC-T cells for 20 hours. Transfection efficiency was measured as the number of blue cells, after X-gal staining 48–60 hours post-transfection, divided by the total number of cells. As is indicated in Table 1, at the optimal charge ratio of 1, the DODAC:DOPE lipid was 5-6-fold more effective than LIPOFECTAMINE™ in transfecting MAC-T cells, however, both lipids are useful in the invention.

TABLE 1

| Lipid | Transfection efficiency % (± SD) |
|---|---|
| DODAC:DOPE (charge ratio of lipid:DNA) | |
| Ratio 0.5 | 20.6 ± 7.3 |
| 1 | 46.1 ± 3.9 |
| 1.5 | 12.3 ± 4.61 |
| 2 | 8.3 ± 2.36 |
| 3 | 3.1 |
| LIPOFECTAMINE ™ (ratio of DNA/lipid; µg/µg) | |
| Ratio 1/6 | 6.34 ± 0.4 |
| 1/5 | 7.47 ± 2.6 |
| 1/4 | 2.58 ± 1.6 |
| 1/3 | 3.86 ± 0.3 |

To assess the dose response ratios in vivo and the effectiveness of DODAC:DOPE in gene transduction, DNA/lipid complexes were infused into the mammary glands of three heifers. In this case, three lipid/DNA ratios were tested in separate quarters of the mammary gland of each mammal. The DODAC:DOPE/DNA ratio in each quarter was 0.5, 1.0, or 1.5, with the fourth quarter of each mammal serving as a control. The animals (5–6 months of age) received 150 µg, 300 µg, or 600 µg of pJ7-hGH (FIG. 1) in 5% dextrose. Infusions and hormonal inductions were performed as is described above. An analysis of milk from one animal indicated that the milk contained 5–7 ng/ml of hGH, as measured by ELISA, on the first day of lactation. This animal was re-induced approximately one month after the first induction, and the milk then contained ~10 ng/ml of hGH, as measured by ELISA, on the first day of lactation. This result indicates that the pJ7-hGH DNA construct persisted within the mammary epithelial cells and/or that it had been incorporated into mammary stem-cells.

Example IV.

Expression of Human Tissue Plasminogen Activator (tPA) in Bovine Mammary Gland: This example describes the expression of human tissue plasminogen activator (tPA) and its secretion into the milk of heifers.

Figure 3:
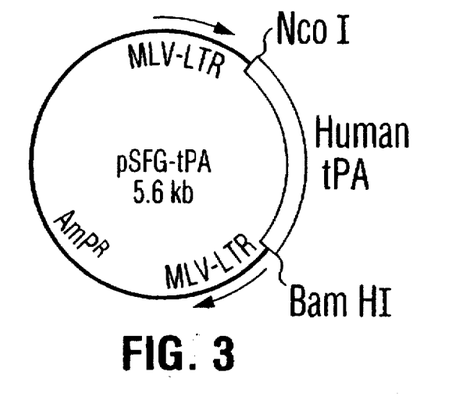
FIG. 3 is a schematic representation of pSFG-tPA.

Plasmid Construction: Plasmid pSFG-tPA included cDNA encoding human tPA under the transcriptional control of the Moloney Murine Leukemia Virus long terminal repeat promoter (MLV-LTR) as is shown in FIG. 3. The plasmid DNA was transfected into MAC-T cells using the lipofection protocols described above. The supernatants from transfected and non-transfected (control) cell cultures were assayed by ELISA for the presence of htPA. The amount of htPA present in the media 48 hours after transfection was approximately 40.3±2.7 ng/ml. Detection of htPA in the media indicates that the genetic construct was able to direct the expression and secretion of htPA in bovine mammary epithelial cells.

Assay System for htPA in Milk: Plasmid pSFG-tPA was infused into the mammary glands of six heifers, and the heifer milk was tested for secretion of htPA. Infusion and induction methods were similar to those described above for expression of hGH in heifers. Milk was removed from the cows by hand, skimmed by centrifugation, and stored at −70° C. until it was assayed. Skim milk was analyzed by ELISA for the presence of htPA. Interference by milk in the assay was tested by establishing a standard curve using the same dilutions of plasma in milk. Skim milk was added to a micro-test well that was coated with goat anti-tPA IgG, and the sample was incubated at 37° C. to permit the capture of htPA within the sample. Horse radish peroxidase labelled anti-tPA IgG (Fab) which binds to captured antigen was then added. After washing, the peroxidase substrate, $OPD/H_2O_2$ was added, and the amount of yellow color was found to be directly proportional to the quantity of htPA present in the sample. One out of six animals that received the SFG-tPA construct expressed 1 to 3 ng tPA/ml milk for at least 5 days. These results indicate that the invention can be used to successfully produce a heterologous protein in the milk of a ruminant mammal.

Example V.

Expression of Human Placental β-galactosidase in MAC-T cells: To direct secretion of β-galactosidase from bovine mammary epithelial cells, an expression vector was constructed which encoded human placental β-galactosidase, a β-galactosidase which contains a signal peptide. To assess the usefulness of this genetic construct, we assayed whether this protein could be secreted from MAC-T cells, the established model system for the ruminant mammary gland.

Figure 4:
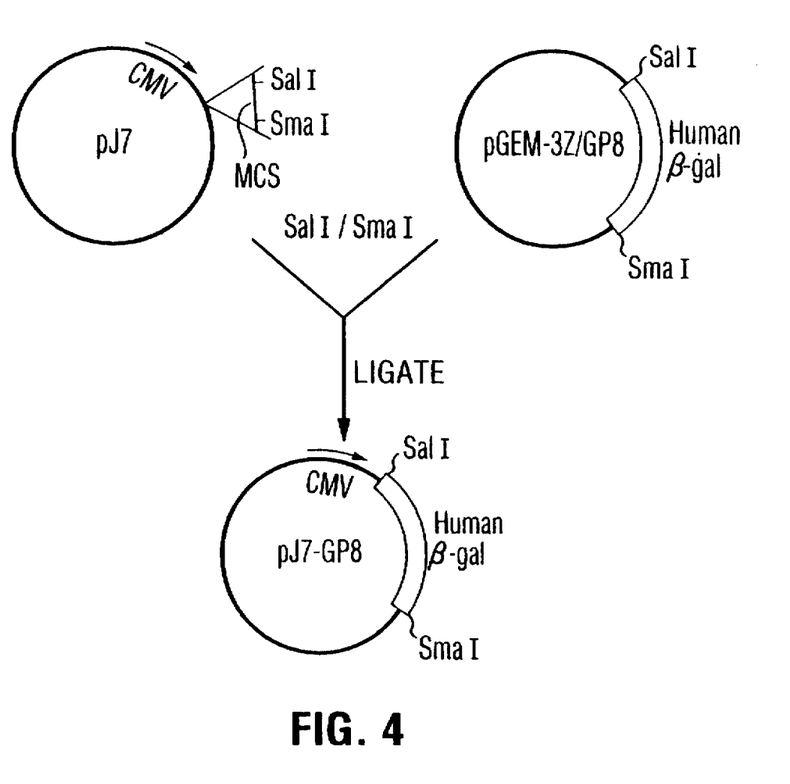
FIG. 4 is a schematic representation of the construction of pJ7-GP8.

The plasmid containing the 2.4 Kb human placental β-galactosidase cDNA, pGEM-3Z/GP8 (Oshima, et al., 1988, Biochem. Biophys. Res. Comm. 157:238) was digested with the restriction enzymes SalI and DraI. The cDNA was purified using gel electrophoresis and conventional extraction procedures. The human placental β-galactosidase cDNA fragment was then ligated directly into the SalI and SmaI sites of plasmid pJ7 (from Dr. G. Matlaslewski, McGill University, Montreal). Plasmid pJ7 has SalI and SmaI sites within its multiple cloning site, and insertion of the β-galactosidase cDNA at these sites places the gene under the transcriptional control of the cytomegalovirus (CMV) early promoter. The resulting construct was termed pJ7-GP8 and its construction is outlined in FIG. 4.

Plasmid pJ7-GP8 was transfected into MAC-T cells using the lipid-based technique described above. It is preferred that no β-galactosidase activity from sources other than the genetic construct be present in the media. Accordingly, media containing heat-inactivated (1 hour at 60° C.) fetal calf serum was used. The conditioned media from the transfected cells was harvested 72 hours after transfection and assayed for β-galactosidase activity using the fluorogenic substrate 4-methylumbeliferyl β-galactoside (Hubbes, et al., 1992, Biochem. J. 285:827). In this assay, it was determined that 139 nmol per minute of substrate was hydrolyzed by the β-galactosidase in the supernatant of transfected cells. There was no detectable activity in the control supernatant from non-transfected cells. These data demonstrate that biologically active β-galactosidase can be produced in, and secreted from, bovine mammary epithelial cells. This observation, in conjunction with the fact that the MAC-T cells represent a suitable model system for the ruminant mammary gland, indicates that genetic constructs which direct production of β-galactosidase in milk can be successfully produced.

Other Embodiments

Other embodiments are within the following claims.

For example, a wide variety of heterologous proteins can be produced in the milk of ruminants using the invention. For example, β-galactosidases other than the human β-galactosidase can be produced. In addition, therapeutically useful proteins other than hGH and htPA can be produced. If desired, more than one heterologous gene product (e.g., a protein, tethered enzyme, ribozyme, and/or antisense oligonucleotide) can be produced in the ruminant. Where two or more heterologous gene products are expressed, the genes can reside on separate plasmids; on one plasmid, with each gene under its own unique promoter; or on one plasmid, with one promoter driving expression of each gene (i.e., internal initiation). For example, genetic constructs encoding β-galactosidase from *Bacillus subtilis* or encoding human placental β-galactosidase can be infused into the ductal tree of the mammal. The expression of these two enzymes enhances hydrolysis of lactose over a wide temperature range. The invention can also be used to produce in one cell a secreted heterologous protein and a tethered heterologous protein in the ruminant mammary gland. Two or more proteins can be produced in the same cell, or the proteins can be produced in different cells.

The invention can also be used in conjunction with other methods of expressing heterologous genes in ruminant mammary glands. For example, transgenic animals produced by introduction of the transgene into a ruminant embryo can be used in the invention. If desired, the heterologous protein produced with this invention can be enzymatically active on a protein produced by the transgene. For example, the invention can be used to express a glycosyl transferase which glycosylates the product of the transgene.

If desired, the lipids and polycationic compounds can be used in combination. For example, a polycationic compound (s) can be used with a lipid compound(s) (e.g., polyornithine and DOTAP), two or more lipid preparations may be used together (e.g., DODAC and DOTMA), or a mixture of polycationic compounds can be used (e.g., poly-lysine and poly-ornithine).

What is claimed is:

1. A method for producing, in a ruminant mammal, milk containing a heterologous protein, said method comprising:

(a) providing a genetic construct including DNA encoding said heterologous protein and a signal peptide, (b) mixing said construct with a liquid carrier to form a liquid complex, (c) infusing said liquid complex into a ductal tree of said mammal at an age of said mammal earlier than sexual maturity and after development of a functional streak canal leading to said ductal tree, (d) raising said mammal so that the mammal lactates and the heterologous protein encoded by said construct is expressed and secreted into the milk produced by said ductal tree and mammary alveolar cells, and (e) obtaining milk from said mammal.

2. The method of claim 1, wherein said mammal is bovine.

3. The method of claim 1, wherein said mammal is a sheep.

4. The method of claim 1, wherein said mammal is a goat.

5. The method of claim 1, wherein said heterologous protein is enzymatically active on a component of milk.

6. The method of claim 5, wherein said heterologous protein is β-galactosidase which hydrolyzes at least 5% of the lactose in said milk.

7. The method of claim 6, wherein the gene encoding said β-galactosidase is derived from an organism selected from the group consisting of *Aspergillus niger, Bacillus stearothermophilus, Escherichia coli, Homo sapiens, Kluyveromyces lactis, Lactobacillus bulgaricus, Streptococcus thermophilus, Streptomyces lividans, Bacillus subtilis* and *Sulfolobus solfataricus*.

8. The method of claim 1, wherein said heterologous protein is human tissue plasminogen activator.

9. The method of claim 1, wherein said heterologous protein is human growth hormone.

10. The method of claim 1, wherein said heterologous protein is selected from the group of proteins consisting of cytokines, aspartic proteases, lysozyme, stearyl-CoA desaturase, lipases, galactosyltransferase, blood clotting proteins, protein C, α1-antitrypsin, urokinase plasminogen activator, human serum albumin, cystic fibrosis transmembrane conductance regulator, gamma-interferon, human CD4, growth factors, peptide hormones, oncoproteins, tumor suppressor proteins, milk proteins, hormone receptors, translation factors, and transcription factors.

11. The method of claim 1, wherein said genetic construct is treated to enhance its ability to cross the membrane of an epithelial cell.

12. The method of claim 11, wherein said treatment of said genetic construct comprises forming a complex between said genetic construct and a polycationic compound.

13. The method of claim 12, wherein said polycationic compound is selected from the group consisting of poly-lysine and poly-ornithine.

14. The method of claim 11, wherein said treatment of said genetic construct comprises forming a complex between said genetic construct and a lipid.

15. The method of claim 14, wherein said lipid is cationic.

16. The method of claim 15, wherein said lipid is selected from the group consisting of dioleyldimethylammonium chloride; 1,2-bis-oleoyloxy-3-trimethylammoniopropane; 1,2-dioleyl-3-N,N,N-trimethylaminopropane; dioleoylphosphatidylethanolamine; 3β [N-(N',N'-dimethylaminoethane)-carbamoyl]cholesterol hydrochloride; dimethyl dioctadecyl ammonium bromide; 2,3-dioleyloxy-N-[2 (sperminecarboxamido)ethyl]-N,N-dimethyl-1-propanaminium tri-fluoroacetate; cholesterol; DL-1,2-dioleoyl-3-dimethylaminopropyl-β-hydroxyethylammonium; and DL-1,2-O-dioleyl-3-dimethylaminopropyl-β-hydroethylammonium.

17. The method of claim 1, wherein mammogenesis and lactogenesis are hormonally induced in said mammal prior to infusion of said liquid complex into said ductal tree.

18. The method of claim 1, wherein, prior to infusion of said genetic construct, said ruminant mammal is treated with a compound selected from the group consisting of EGTA, EDTA, chloroquine, and colchicine.

19. The method of claim 1, wherein said liquid complex is free of live retroviruses.

20. A method of producing, in a ruminant mammal, milk containing a heterologous protein, said method comprising:

(a) providing a genetic construct including DNA encoding said heterologous protein and a signal peptide, (b) mixing said construct with a liquid carrier to form a liquid complex free of live retroviruses, (c) infusing said liquid complex into a ductal tree of said mammal, (d) raising said mammal so that the mammal lactates and the heterologous protein encoded by said construct is expressed and secreted into the milk produced by said ductal tree and mammary alveolar cells, and (e) obtaining said milk from said mammal.

21. The method of claim 20, wherein said mammal is bovine.

22. The method of claim 20, wherein said mammal is a sheep.

23. The method of claim 20, wherein said mammal is a goat.

24. The method of claim 20, wherein said heterologous protein is enzymatically active on a component of milk.

25. The method of claim 20, wherein said heterologous protein is β-galactosidase which hydrolyzes at least 54% of the lactose in said milk.

26. The method of claim 20, wherein said genetic construct is treated to enhance its ability to cross the membrane of an epithelial cell.

27. The method of claim 20, wherein mammogenesis and lactogenesis are hormonally induced in said mammal prior to infusion of said liquid complex into said ductal tree.

28. The method of claim 26, wherein said treatment of said genetic construct comprises forming a complex between said genetic construct and a polycationic compound.

29. The method of claim 20, wherein said liquid complex is infused into said ductal tree at an age of said mammal earlier than sexual maturity and after development of a functional streak canal leading to said ductal tree.

30. A method for expressing, in the mammary gland of a ruminant mammal, a heterologous enzyme which is tethered to the membrane of an epithelial cell of said mammary gland, said method comprising:

(a) providing a genetic construct encoding said heterologous enzyme and a membrane-associated polypeptide, (b) mixing said construct with a liquid carrier to form a liquid complex, (c) infusing said liquid complex into a ductal tree of said mammal at an age of said mammal earlier than sexual maturity and after development of a functional streak canal leading to said ductal tree, (d) raising said mammal so that said heterologous enzyme is expressed and becomes associated with said membrane.

31. The method of claim 30, wherein said heterologous enzyme modifies the carbohydrate content of said milk.

32. The method of claim 31, wherein said heterologous enzyme is β-galactosidase which hydrolyzes at least 5% of the lactose in said milk.

33. The method of claim 30, further comprising raising the mammal so that the mammal lactates and milk is produced and obtaining said milk from said mammal.

34. The method of claim 33, wherein said heterologous enzyme modifies the protein content of said milk.

35. The method of claim 33, wherein said heterologous enzyme modifies the lipid content of said milk.

36. The method of claim 33, wherein said genetic construct encodes a signal peptide.

37. A method for determining whether a heterologous gene is expressed in the mammary gland of a ruminant mammal, said method comprising:

(a) providing a genetic construct including said heterologous gene, (b) mixing said construct with a liquid carrier to form a liquid complex, (c) infusing said liquid complex into a ductal tree of said mammal at an age of said mammal earlier than sexual maturity and after development of a functional streak canal leading to said ductal tree, and (d) assaying for expression of said heterologous gene.

38. The method of claim 37, wherein said heterologous gene encodes a heterologous protein.

39. The method of claim 37, further comprising raising the mammal so that the mammal lactates and the heterologous protein is secreted into milk produced by said ductal tree and mammary alveolar cells.

40. The method of claim 39, further comprising obtaining milk from said mammal.

41. The method of claim 39, further comprising detecting the heterologous protein in the milk.

* * * * *